(12) United States Patent
Candau

(10) Patent No.: US 7,291,322 B2
(45) Date of Patent: Nov. 6, 2007

(54) PHOTOPROTECTING/COSMETIC COMPOSITIONS COMPRISING BENZOTRIAZOLE AND BIS-RESORCINYLTRIAZINE

(75) Inventor: Didier Candau, Bièvres (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 11/529,618

(22) Filed: Sep. 29, 2006

(65) Prior Publication Data

US 2007/0020204 A1    Jan. 25, 2007

Related U.S. Application Data

(63) Continuation of application No. 10/855,350, filed on May 28, 2004, now abandoned, which is a continuation of application No. 09/927,488, filed on Aug. 13, 2001, now abandoned, which is a continuation of application No. PCT/FR00/00257, filed on Feb. 3, 2000.

(30) Foreign Application Priority Data

Feb. 12, 1999   (FR) .................................. 99 01729

(51) Int. Cl.
- *A61Q 17/04* (2006.01)
- *A61Q 19/00* (2006.01)
- *A61K 8/00* (2006.01)

(52) U.S. Cl. .......................... 424/59; 424/60; 424/400; 424/401

(58) Field of Classification Search ................ 424/59, 424/60, 400, 401
See application file for complete search history.

(56) References Cited

U.S. PATENT DOCUMENTS

| | | | |
|---|---|---|---|
| 4,247,411 A | 1/1981 | Vanlerberghe et al. | |
| 4,316,033 A | 2/1982 | Ching | |
| 4,328,346 A | 5/1982 | Chung et al. | |
| 5,089,250 A | 2/1992 | Forestier et al. | |
| 5,102,707 A | 4/1992 | Canivenc et al. | |
| 5,597,854 A | 1/1997 | Birbaum et al. | |
| 5,618,520 A | 4/1997 | Hansenne et al. | |
| 5,753,209 A | 5/1998 | Ascione et al. | |
| 5,955,060 A | 9/1999 | Hüglin et al. | |
| 5,962,452 A | 10/1999 | Hasse et al. | |
| 6,030,629 A | 2/2000 | Hansenne | |
| 6,171,579 B1 | 1/2001 | Allard et al. | |
| 6,251,373 B1 | 6/2001 | Candau | |

FOREIGN PATENT DOCUMENTS

| | | |
|---|---|---|
| EP | 0 517 104 A1 | 12/1992 |
| EP | 0 518 772 A1 | 12/1992 |
| EP | 0 518 773 A1 | 12/1992 |
| EP | 0 392 883 B1 | 4/1993 |
| EP | 0 354 145 B1 | 11/1993 |
| EP | 0 570 838 A1 | 11/1993 |
| EP | 0 711 804 A2 | 5/1996 |
| EP | 0 775 698 A1 | 5/1997 |
| EP | 0 660 701 B1 | 6/1997 |
| EP | 0 742 003 B1 | 9/1997 |
| EP | 0 796 851 A1 | 9/1997 |
| EP | 0 863 145 A2 | 9/1998 |
| EP | 0 878 469 A1 | 11/1998 |
| FR | 2315991 A1 | 1/1977 |
| FR | 2416008 A1 | 8/1979 |
| GB | 1539625 A | 1/1979 |
| WO | WO 93/04665 A1 | 3/1993 |
| WO | WO 98/22447 A1 | 5/1998 |
| WO | WO 98/23252 A1 | 6/1998 |
| WO | WO 99/08653 A1 | 2/1999 |

OTHER PUBLICATIONS

Bangham, A. D. et al., "*Diffusion of Univalent Ions across the Lamellae of Swollen Phospholipids*," 13 J. Mol. Biol., 238-252 (1965), Academic Press, London.

*Primary Examiner*—Shelley A. Dodson
(74) *Attorney, Agent, or Firm*—Buchanan, Ingersoll & Rooney, PC

(57) ABSTRACT

Topically applicable sunscreen/cosmetic compositions suited for the improved photoprotection of human skin and/or hair against the damaging effects of UV-irradiation, particularly solar radiation, comprise an effective SPF-maintaining and water remanence-enhancing amount of intimate admixture of (a) at least one benzotriazole first sunscreen compound and (b) at least one bis-resorcinyltriazine second sunscreen compound, formulated into (c) a topically applicable, cosmetically acceptable vehicle, diluent or carrier therefor.

16 Claims, No Drawings

PHOTOPROTECTING/COSMETIC COMPOSITIONS COMPRISING BENZOTRIAZOLE AND BIS-RESORCINYLTRIAZINE

CROSS-REFERENCE TO EARLIER APPLICATIONS

This application is a continuation of U.S. application Ser. No. 10/855,350, filed May 28, 2004 now abandoned, which is a continuation of U.S. application Ser. No. 09/927,488, filed Aug. 13, 2001, now abandoned, said application Ser. No. 09/972,488 claiming priority under 35 U.S.C. § 119 of FR-99/01729, filed Feb. 12, 1999, and being a continuation of International Application No. PCT/FR00/00257, filed Feb. 3, 2000 and designating the United States (published in the French language on Aug. 17, 2000 as WO 00/47176; the title and abstract were also published in English), all hereby expressly incorporated by reference.

BACKGROUND OF THE INVENTION

1. Technical Field of the Invention

The present invention relates to novel cosmetic compositions for topical application, for photoprotecting the skin and/or the hair against the deleterious effects of ultraviolet radiation (such compositions hereinbelow more simply referred to as antisun or sunscreen compositions), and to the use of same for the cosmetic applications indicated above.

This invention more especially relates to the aforesaid sunscreen/cosmetic compositions comprising, formulated into a cosmetically acceptable support (vehicle, diluent or carrier), admixture of (a) a benzotriazole compound first screening agent and (b) a specific bis-resorcinyltriazine compound second screening agent.

2. Description of the Prior Art

It is known to this art that light radiation with wavelengths of from 280 nm to 400 nm promotes tanning of the human epidermis, and that irradiation with wavelengths of from 280 nm to 320 nm, i.e., UV-B radiation, causes skin burns and erythema which may be harmful to the development of a natural tan; this UV-B radiation should thus be screened from the skin.

It is also known to this art that UV-A radiation, with wavelengths of from 320 nm to 400 nm, which causes tanning of the skin, can also induce an adverse change therein, especially in the case of sensitive skin or of skin which is continually exposed to solar radiation. UV-A rays cause, in particular, a loss of elasticity of the skin and the appearance of wrinkles, leading to premature skin aging. Such irradiation promotes triggering of the erythemal reaction or amplifies this reaction in certain individuals and may even be the cause of phototoxic or photoallergic reactions. It is thus desirable to also screen out UV-A radiation.

A wide variety of cosmetic compositions for the photoprotection (UV-A and/or UV-B) of human skin are known to this art.

These antisun/sunscreen compositions are quite often in the form of an emulsion of oil-in-water type (namely, a cosmetically acceptable vehicle comprising a continuous aqueous dispersing phase and a discontinuous oily dispersed phase) which contains, in various concentrations, one or more conventional lipophilic and/or hydrophilic organic screening agents which are capable of selectively absorbing harmful UV radiation. These screening agents (and their amounts) are selected as a function of the desired sun protection factor (the sun protection factor (SPF) which is expressed mathematically by the ratio of the irradiation time necessary to attain the erythemogenic threshold with the UV screening agent to the time necessary to attain the erythemogenic threshold without UV screening agent).

EP-B-0,742,003 describes antisun/cosmetic compositions having high sun protection factors; these compositions comprise a combination of two sunscreens, namely, (a) benzene-1,4-bis(3-methylidene-10-camphorsulfonic acid), optionally in partially or totally neutralized form, as a first screening agent, and (b), as a second screening agent, a benzotriazole silicone such as those described in EP-B-0,660,701. However, these sunscreen/photoprotecting products are usually considered to possess insufficient water remanence.

SUMMARY OF THE INVENTION

It has now surprisingly and unexpectedly been determined that intimate admixture of (a) at least one benzotriazole compound as a first screening agent and (b) at least one specific bis-resorcinyltriazine compound as a second screening agent provides sunscreen/photoprotecting compositions whose water remanence is substantially improved, while at the same time having a level of sun protection which is as high as that of the above-indicated photoprotective compositions of the prior art.

Briefly, the present invention features novel cosmetic or dermatological, in particular antisun/sunscreen, compositions which are essentially characterized in that they comprise, formulated into a cosmetically acceptable support, (a) as a first screening agent, at least one benzotriazole compound of formula (I) below:

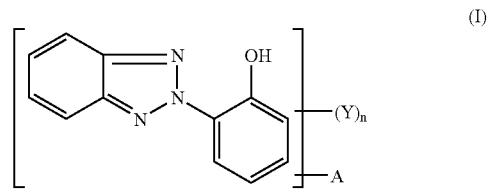

in which A is a hydrogen atom or a divalent radical -L-W—; the radicals Y, which may be identical or different, are each a $C_1$-$C_{10}$ alkyl radical, a halogen atom, a $C_1$-$C_{10}$ alkoxy radical or a sulfonic group, with the proviso that, in the latter case, two adjacent Y radicals on the same aromatic nucleus can together form an alkylidenedioxy group in which the alkylidene moiety has 1 or 2 carbon atoms; with the further proviso that the radicals Y are other than a sulfonic group when A is other than a hydrogen atom; n is 1, 2, or 3; L is a divalent radical of formula (II) below:

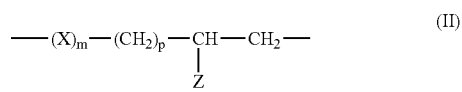

in which X is O or NH; Z is a hydrogen atom or a $C_1$-$C_4$ alkyl radical; n is an integer ranging from 0 to 3, inclusive, m is 0 or 1; p is an integer ranging from 1 to 10, inclusive; W is a radical of formula (1), (2) or (3) below:

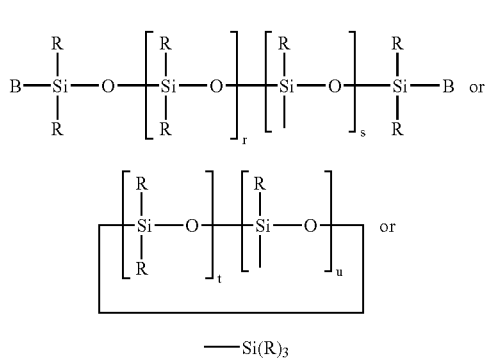

in which the radicals R, which may be identical or different, are each a $C_1$-$C_{10}$ alkyl, phenyl or 3,3,3-trifluoropropyl radical, at least 80%, by number, of the radicals R being methyl radicals; the radicals B, which may be identical or different, are each a radical R or the radical V having the following formula:

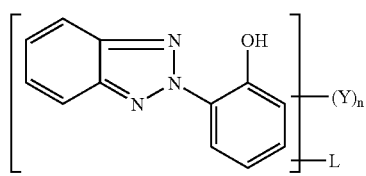

in which Y, n and L are as defined above; r is an integer ranging from 0 to 50, inclusive, and s is an integer ranging from 1 to 20, inclusive, and, if s=0, then at least one of the two radicals B is a radical V; u is an integer ranging from 1 to 6, inclusive, and t is an integer ranging from 0 to 10, inclusive, with the proviso that t+u is greater than or equal to 3; and (b), as a second screening agent, at least one bis-resorcinyltriazine compound having the formula (III) below:

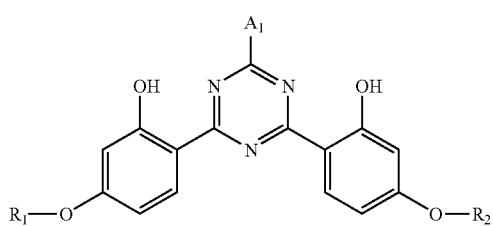

in which (i) the radicals $R_1$ and $R_2$, which may be identical or different, are each a $C_3$-$C_{18}$ alkyl radical, a $C_2$-$C_{18}$ alkenyl radical, or a residue of formula —$CH_2$—CH(OH)—$CH_2$—$OT_1$ wherein $T_1$ is a hydrogen atom or a $C_1$-$C_8$ alkyl radical; or (ii) the radicals $R_1$ and $R_2$, which again may be identical or different, can also be a residue of formula (4) below:

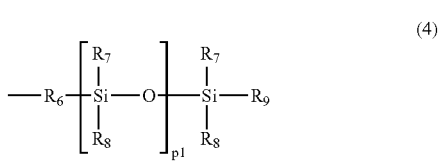

in which $R_6$ is a covalent bond, a linear or branched $C_1$-$C_4$ alkyl radical, or a residue of formula —$C_{m1}H_{2m1}$— or —$C_{m1}H_{2m1}$—O— wherein $m_1$ is a number ranging from 1 to 4; $p_1$ is a number ranging from 0 to 5; the radicals $R_7$, $R_8$ and $R_9$, which may be identical or different, are each a $C_1$-$C_{18}$ alkyl radical, a $C_1$-$C_{18}$ alkoxy radical, or a residue of formula (5) below:

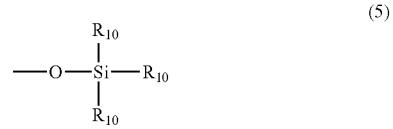

in which $R_{10}$ is a $C_1$-$C_5$ alkyl radical; $A_1$ is a residue having one of the following formulae (6), (7) or (8):

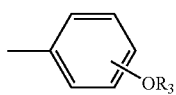

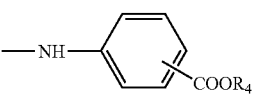

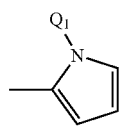

in which $R_3$ is a hydrogen atom, a $C_1$-$C_{10}$ alkyl radical, a radical of formula —$(CH_2CHR_5$—$O)_{n1}R_{11}$ wherein $n_1$ is a number ranging from 1 to 16, $R_{11}$ is a hydrogen atom, a methyl radical, or a residue of the formula —$CH_2$—CH—(OH)—$CH_2OT_1$ wherein $T_1$ is as defined above; $R_4$ is a hydrogen atom; a metal cation M, a $C_1$-$C_5$ alkyl radical, or a residue of formula —$(CH_2)m_2$—$OT_1$ wherein $m_2$ is a number ranging from 1 to 4 and $T_1$ is as defined above; and $Q_1$ is a $C_1$-$C_{18}$ alkyl radical.

The present invention also features the manufacture of cosmetic compositions for protecting the skin and/or the hair against ultraviolet radiation, in particular solar radiation.

Too, the present invention features a cosmetic regime/regimen for protecting the skin and/or the hair against ultraviolet radiation, in particular solar radiation, and which comprises topically applying an effective amount of a subject composition onto the skin and/or the hair.

DETAILED DESCRIPTION OF BEST MODE AND SPECIFIC/PREFERRED EMBODIMENTS OF THE INVENTION

More particularly according to the present invention, the subject benzotriazole compounds of formula (I) are UV-screening agents that are per se known to this art. These are described and prepared according to the syntheses indicated in U.S. Pat. Nos. 4,316,033 and 4,328,346; EP-B-0,354,145, EP-B-0,392,883 and EP-B-0,660,701 hereby expressly incorporated by reference.

Among the non-silicone compounds of formula (I) in which A is a hydrogen atom according to the invention, particularly exemplary are:

2-(2'-hydroxy-5'-methylphenyl)benzotriazole (n=1 and Y=$CH_3$), such as the product marketed under the trademark Uvazol P by Enichem Synth and the product marketed under the trademark Tinuvin P by Ciba Geigy;

2-(2'-hydroxy-3'-butyl-5'-methylphenyl)benzotriazole (n=2 and Y=$CH_3$ and —$C(CH_3)_3$), such as the product marketed under the trademark Uvazol 236 by Enichem Synth;

2-(2'-hydroxy-5'-t-octylphenyl)benzotriazole (n=1 and Y=—$C(CH_3)_2$—$CH_2$—$C(CH_3)_3$), such as the product marketed under the trademark Uvazol 311 by Enichem Synth;

2-(2'-hydroxy-3'-sec-butyl-5'-benzenesulfonato)benzotriazole (n=2 and Y=$SO_3H$; Y=—$CH(CH_3)$—$CH_2$—$CH_3$), such as the product marketed under the trademark Cibafast by Ciba Geigy.

For the silicone compounds of formula (I) in which A is a divalent radical -L-W—, in the definition of formulae (1), (2) and (3) as defined above, the alkyl radicals may be linear or branched and are selected, in particular, from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. The alkyl radicals R that are preferred according to the invention are methyl, ethyl, propyl, n-butyl, n-octyl and 2-ethylhexyl radicals. Even more preferably, the radicals R are all methyl radicals.

For the silicone compounds of formula (I) in which A is a divalent radical -L-W—, it is preferred to employ those in which W corresponds to formula (1), i.e., diorganosiloxanes containing a linear chain.

Among the linear diorganosiloxanes according to the present invention, those more particularly preferred are the random derivatives or the derivatives well-defined in blocks having at least one, and more preferably all, of the following characteristics:

R is an alkyl radical and even more preferably is a methyl radical;

B is an alkyl radical and even more preferably is a methyl radical;

r ranges from 0 to 15, inclusive; s ranges from 1 to 5, inclusive;

n is other than zero and preferably is equal to 1, and Y is then selected from among methyl, tert-butyl and $C_1$-$C_4$ alkoxy;

Z is a hydrogen atom or a methyl radical;

m=0 or [m=1 and X=O];

p is equal to 1.

As will be seen from formula (I) above, the bonding of the divalent radical —$(X)_m$—$(CH_2)_p$—$CH(Z)$—$CH_2$— to the benzotriazole structural unit, which thus links said benzotriazole unit to the silicon atom of the silicone backbone, can, according to the present invention, be at any of the available positions presented by the two aromatic nuclei of the benzotriazole:

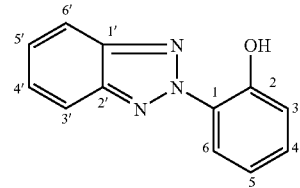

Preferably, this attachment is at position 3-, 4-, 5-(aromatic nucleus bearing the hydroxyl function) or 4'-(benzene nucleus adjacent to the triazole ring), and even more preferably at position 3-, 4- or 5-. In one preferred embodiment of the invention, the attachment is at position 3-.

Similarly, the attachment of the substituent Y can be at any of the other positions available on the benzotriazole. However, this attachment preferably is at position 3-, 4-, 4'-, 5- and/or 6-. In one preferred embodiment of the invention, the attachment is at position 5-.

One family of compounds which is particularly suitable for the invention is that having the following general formula (I'):

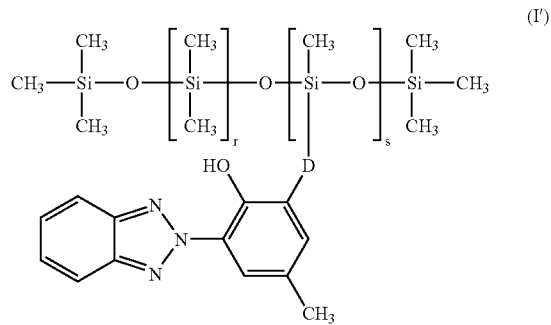

in which $0 \leq r \leq 15$, preferably $0 \leq r \leq 10$, $1 \leq s \leq 5$, preferably $1 \leq s \leq 3$, and in which D represents the divalent radical:

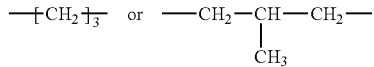

In one particularly preferred embodiment of the invention, the benzotriazole silicone has the structural formula (I') in which:

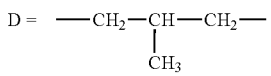

In another particularly preferred embodiment of the invention, the benzotriazole silicone has the structural formula (I') in which:

r = 0
s = 1
D = 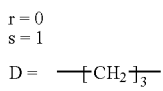

The benzotriazole compounds of formula (I) are advantageously present in amounts of from 0.1% to 15% and preferably from 0.2% to 10% by weight, relative to the total weight of the composition.

In formulae (III) and (4) to (8) described above:
the alkyl radicals are linear or branched and are selected, for example, from among methyl, ethyl, n-propyl, isopropyl, n-butyl, sec-butyl, tert-butyl, amyl, isoamyl, tert-amyl, heptyl, octyl, isooctyl, nonyl, decyl, undecyl, dodecyl, tetradecyl, pentadecyl, hexadecyl, heptadecyl and octadecyl radicals;
the alkenyl radicals are selected, for example, from among allyl, methylallyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl and n-octadec-4-enyl radicals;
the alkoxy radicals are linear or branched and are selected, for example, from among methoxy, ethoxy, n-propoxy, isopropoxy, n-butoxy, sec-butoxy, tert-butoxy, amyloxy, isoamyloxy and tert-amyloxy radicals;
the $C_1$-$C_5$ mono- or dialkylamino radicals are selected, for example, from among methylamino, ethylamino, propylamino, n-butylamino, sec-butylamino, tert-butylamino, pentylamino, dimethylamino, diethylamino, dibutylamino and methylethylamino radicals;
the metal cations are preferably alkali metal or alkaline earth metal cations or metallic cations selected, for example, from among lithium, potassium, sodium, calcium, magnesium, copper and zinc cations.

The bis-resorcinyltriazine compounds of formula (III) of the invention are UV-screening agents that are also per se known to this art. These are described and prepared according to the syntheses indicated in EP-A-0,775,698 hereby expressly incorporated by reference.

Exemplary compounds of formula (III) include:
2,4-bis{[4-(2-ethylhexyloxy)-2-hydroxy]phenyl}-6-(4-methoxyphenyl)-1,3,5-triazine;
2,4-bis{[4-(3-(2-propyloxy)-2-hydroxypropyloxy)-2-hydroxy]phenyl}-6-(4-methoxyphenyl)-1,3,5-triazine;
2,4-bis{[4-(2-ethylhexyloxy)-2-hydroxy]phenyl}-6-[4-(2-methoxyethylcarboxyl)phenylamino]-1,3,5-triazine;
2,4-bis{[4-(tris(trimethylsiloxy)silylpropyloxy)-2-hydroxy]phenyl}-6-(4-methoxyphenyl)-1,3,5-triazine;
2,4-bis{[4-(2"-methylpropenyloxy)-2-hydroxy]phenyl}-6-(4-methoxyphenyl)-1,3,5-triazine;
2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine;
2,4-bis{[4-(3-(2-propyloxy)-2-hydroxypropyloxy)-2-hydroxy]phenyl}-6-[4-(ethoxycarbonyl)phenylamino]-1,3,5-triazine;
2,4-bis{[4-(2-ethylhexyloxy)-2-hydroxy]phenyl}-6-(1-methylpyrrol-2-yl)-1,3,5-triazine.

The compounds derived from bis-resorcinyltriazine that are more particularly preferred according to the invention are selected from the group consisting of:
2,4-bis{[4-(2-ethylhexyloxy)-2-hydroxy]phenyl}-6-(4-methoxyphenyl)-1,3,5-triazine;
2,4-bis{[4-(tris(trimethylsiloxy)silylpropyloxy)-2-hydroxy]phenyl}-6-(4-methoxyphenyl)-1,3,5-triazine;
2,4-bis{[4-(1',1',1',3',5',5',5'-heptamethyltrisiloxy-2"-methylpropyloxy)-2-hydroxy]phenyl}-6-(4-methoxyphenyl)-1,3,5-triazine.

The sunscreen(s) of the bis-resorcinyltriazine compound type of formula (III) are advantageously present in the compositions according to the invention at a concentration of from 0.1% to 15% and preferably from 0.2% to 10% by weight relative to the total weight of the composition.

In addition and in general, it should be appreciated that the concentrations and ratios of benzotriazole compounds of formula (I) and of bis-resorcinyltriazine compounds of formula (III) as described above are selected such that the sun protection factor of the final composition is preferably at least 2.

In another preferred embodiment of the present invention, the cosmetically acceptable support in which the various types of screening agent are formulated is an emulsion of oil-in-water type.

It will of course be appreciated that the antisun/sunscreen cosmetic compositions according to the invention can contain one or more additional hydrophilic or lipophilic UVA-active and/or UVB-active sunscreen(s) (absorbers) other than the subject two screening agents. These additional screening agents are advantageously selected, in particular, from among cinnamic derivatives; salicylic derivatives; camphor derivatives; triazine derivatives other than those described above, such as those described in EP-863,145, EP-517,104, EP-570,838 and EP-796,851; benzophenone derivatives; dibenzoylmethane derivatives; β,βN-diphenylacrylate derivatives, benzimidazole derivatives; p-aminobenzoic acid derivatives; screening polymers and screening silicones, such as those described in WO-93/04665.

Exemplary such additional UV-A-active and/or UV-B-active sunscreens include:
p-aminobenzoic acid;
oxyethylenated (25 mol) p-aminobenzoate;
2-ethylhexyl p-dimethylaminobenzoate;
N-oxypropylenated ethyl p-aminobenzoate;
glyceryl p-aminobenzoate;
homomenthyl salicylate;
2-ethylhexyl salicylate;
triethanolamine salicylate;
4-isopropylbenzyl salicylate;
4-tert-butyl-4'-methoxydibenzoylmethane;
4-isopropyldibenzoylmethane;
2-ethylhexyl 4-methoxycinnamate;
methyl diisopropylcinnamate;
isoamyl 4-methoxycinnamate;
diethanolamine 4-methoxycinnamate;
menthyl anthranilate;
2-ethylhexyl 2-cyano-3,3'-diphenylacrylate;
ethyl 2-cyano-3,3'-diphenylacrylate;
2-phenylbenzimidazole-5-sulfonic acid and salts thereof;
3-(4'-trimethylammonio)benzylidenebornan-2-one methyl sulfate;
benzene-1,4-bis(3-methylidene-10-camphorsulfonic acid) and salts thereof;
urocanic acid;
2-hydroxy-4-methoxybenzophenone;
2-hydroxy-4-methoxybenzophenone-5-sulfonate;
2,4-dihydroxybenzophenone;
2,2',4,4'-tetrahydroxybenzophenone;
2,2'-dihydroxy-4,4'-dimethoxybenzophenone;
2-hydroxy-4-n-octoxybenzophenone;
2-hydroxy-4-methoxy-4'-methylbenzophenone;
α-(2-oxoborn-3-ylidene)tolyl-4-sulfonic acid and salts thereof;

3-(4'-sulfo)benzylidenebornan-2-one and salts thereof;
3-(4'-methylbenzylidene)-d,1-camphor;
3-benzylidene-d,1-camphor;
2,4,6-tris[p-(2'-ethylhexyl-1'-oxycarbonyl)anilino]-1,3,5-triazine;
2-[p-(tert-butylamido)anilino]-4,6-bis[(p-(2'-ethylhexyl-1'-oxycarbonyl)anilino]-1,3,5-triazine;
1,4-bis(benzimidazolyl)phenylene-3,3',5,5'-tetrasulfonic acid and salts thereof;
the polymer of N-[(2 and 4)-[(2-oxoborn-3-ylidene)methyl]benzyl]acrylamide;
polyorganosiloxanes containing a malonate functional group.

The compositions according to the invention may also contain agents for the artificial tanning and/or browning of the skin (self-tanning agents) such as, for example, dihydroxyacetone (DHA).

The cosmetic compositions according to the invention may also contain pigments or nanopigments (average size of the primary particles: generally ranging from 5 nm to 100 nm, preferably from 10 nm to 50 nm) of coated or uncoated metal oxides, for example nanopigments of titanium dioxide (amorphous or crystallized in rutile and/or anatase form), of iron oxide, of zinc oxide, of zirconium oxide or of cerium oxide which are all UV-photoprotective agents that are well known to this art. Conventional coating agents include, moreover, alumina and/or aluminum stearate. Such coated or uncoated metal oxide nanopigments are described, in particular, in EP-A-0,518,772 and EP-A-0,518,773.

The compositions of the invention may also comprise conventional cosmetic additives and adjuvants selected, in particular, from among fatty substances, organic solvents, thickeners, softeners, antioxidants, opacifying agents, stabilizers, emollients, hydroxy acids, anti-foaming agents, moisturizers, vitamins, fragrances, preservatives, surfactants, fillers, sequestering agents, polymers, propellants, basifying or acidifying agents, dyes, colorants, or any other ingredient usually formulated into cosmetics, in particular for the manufacture of antisun/sunscreen compositions in the form of emulsions.

The fatty substances may be an oil or a wax or mixtures thereof, and may also be fatty acids, fatty alcohols and fatty acid esters. The oils may be animal, plant, mineral or synthetic oils and, in particular, liquid petrolatum, liquid paraffin, volatile or non-volatile silicone oils, isoparaffins, poly-α-olefins, fluoro oils and perfluoro oils. Similarly, the waxes may be animal, fossil, plant, mineral or synthetic waxes that are per se known to this art.

Among the organic solvents, exemplary are the lower alcohols and polyols.

The thickeners may be selected, in particular, from among crosslinked acrylic acid homopolymers and modified or unmodified guar gums and celluloses such as hydroxypropyl guar gum, methylhydroxyethylcellulose, hydroxypropylmethylcellulose or hydroxyethylcellulose.

One skilled in this art will of course take care to select the optional additional compound or compounds and/or the amounts thereof such that the advantageous properties, in particular the water remanence and the level of photoprotection, intrinsically associated with the binary combination in accordance with the invention, are not, or are substantially not, adversely affected by the addition or additions envisaged.

The compositions of the invention may be prepared according to techniques which are well known to this art, in particular those for formulating emulsions of oil-in-water or water-in-oil type.

Such compositions may be, in particular, in simple or complex emulsion form (O/W, W/O, O/W/O or W/O/W), such as a cream, a milk, a lotion, an ointment, a gel or a cream-gel, a powder or a solid stick and may optionally be packaged as an aerosol and may be in the form of a foam or a spray.

When the composition is an emulsion, the aqueous phase thereof may comprise a nonionic vesicular dispersion prepared according to known processes (Bangham, Standish and Watkins, *J. Mol. Biol.*, 13, 238 (1965), FR-2,315,991 and FR-2,416,008).

The cosmetic compositions of the invention may be for protecting the human skin or the hair against ultraviolet rays, as an antisun/sunscreen composition or as a makeup product.

When the cosmetic compositions according to the invention are for protecting the human epidermis against UV rays or as an antisun/sunscreen composition, same may be in the form of a suspension or dispersion in solvents or in fatty substances, in the form of a nonionic vesicular dispersion or, alternatively, in the form of an emulsion, preferably of oil-in-water type, such as a cream or a milk, or in the form of an ointment, a gel, a cream-gel, a powder, a solid tube, a stick, an aerosol foam or a spray.

When the cosmetic compositions according to the invention are to protect the hair, it may be in the form of a shampoo, a lotion, a gel, an emulsion or a nonionic vesicular dispersion and may constitute, for example, a rinse-out composition to be applied before or after shampooing, before or after dyeing or bleaching, before, during or after permanent-waving or straightening of the hair, a styling or treating lotion or gel, a blow-drying or hair-setting lotion or gel or a composition for permanent-waving, straightening, dyeing or bleaching the hair.

When the composition is used as a makeup product for the eyelashes, the eyebrows or the skin, such as a treatment cream for the epidermis, a foundation, a lipstick, an eyeshadow, a blusher, a mascara or an eyeliner, it may be in anhydrous or aqueous, solid or pasty form, for example oil-in-water or water-in-oil emulsions, nonionic vesicular dispersions or suspensions.

For example, for the antisun/sunscreen formulations in accordance with the invention which have a support of oil-in-water emulsion type, the aqueous phase (in particular comprising the hydrophilic screening agents) generally constitutes from 50% to 95% by weight, preferably from 70% to 90% by weight, relative to the total weight of the formulation, the oily phase (in particular comprising the lipophilic screening agents) from 5% to 50% by weight, preferably from 10% to 30% by weight, relative to the total weight of the formulation, and the (co)emulsifying agent(s) from 0.5% to 20% by weight, preferably from 2% to 10% by weight, also relative to the total weight of the formulation.

As indicated above, the present invention also features a cosmetic regime or regimen for the skin or the hair to protect the skin/hair against the damaging effects of UV irradiation, which comprises topically applying an effective amount of a cosmetic composition as described above onto the skin or the hair.

In order to further illustrate the present invention and the advantages thereof, the following specific examples are given, it being understood that same are intended only as illustrative and in nowise limitative.

EXAMPLE 1

| COMPOSITION | |
|---|---|
| 80/20 Mixture of cetylstearyl alcohol and of oxyethylenated (33 EO) cetylstearyl alcohol (Sinnowax AO - Henkel) | 7 g |
| Mixture of glyceryl mono- and distearate (Cerasynt SD-V - ISP) | 2 g |
| Cetyl alcohol | 1.5 g |
| Polydimethylsiloxane (Dow Corning 200 Fluid - Dow Corning) | 1 g |
| $C_{12}/C_{15}$ Alkyl benzoate (Witconol TN - Witco) | 15 g |
| 2,4-Bis{[4-(2-ethylhexyloxy)-2-hydroxy]phenyl}-6-(4-methoxyphenyl)-1,3,5-triazine | 2 g |
| Benzotriazole silicone of formula (I') in which: r = 0; s = 1 and D = —CH$_2$—CH(CH$_3$)—CH$_2$— | 3 g |
| Glycerol | 15 g |
| Preservatives | qs |
| Demineralized water qs | 100 g |

EXAMPLE 2

| COMPOSITION | |
|---|---|
| Glyceryl mono-/distearate/polyethylene glycol stearate (100 EO) mixture (Arlacel 165 FL - ICI) | 2 g |
| Stearyl alcohol (Lanette 18 - Henkel) | 1 g |
| Stearic acid from palm oil (Stearine TP - Stearinerie Dubois) | 2.5 g |
| Polydimethylsiloxane (Dow Corning 200 Fluid - Dow Corning) | 0.5 g |
| $C_{12}/C_{15}$ Alkyl benzoate (Witconol TN - Witco) | 20 g |
| Triethanolamine | 0.5 g |
| 2,4-Bis{[4-(tris(trimethylsiloxy)silylpropyloxy)-2-hydroxy]phenyl}-6-(4-methoxyphenyl)-1,3,5-triazine | 2.5 g |
| Benzotriazole silicone of formula (I') in which: r = 0; s = 1 and D = —CH$_2$—CH(CH$_3$)—CH$_2$— | 2.5 g |
| Glycerol | 5 g |
| Hexadecyl phosphate, potassium salt (Amphisol K - Hoffman Laroche) | 1 g |
| Polyacrylic acid (Synthalen K - 3V) | 0.3 g |
| Hydroxypropylmethylcellulose (Methocel F4M - Dow Chemical) | 0.1 g |
| Triethanolamine | 0.3 g |
| Preservatives | qs |
| Demineralized water qs | 100 g |

EXAMPLE 3

| COMPOSITION | |
|---|---|
| 80/20 Mixture of cetylstearyl alcohol and of oxyethylenated (33 EO) cetylstearyl alcohol (Sinnowax AO - Henkel) | 7 g |
| Mixture of glyceryl mono- and distearate (Cerasynt SD-V - ISP) | 2 g |
| Cetyl alcohol | 1.5 g |
| Polydimethylsiloxane (Dow Corning 200 Fluid - Dow Corning) | 1 g |
| $C_{12}/C_{15}$ Alkyl benzoate (Witconol TN - Witco) | 15 g |
| 2,4-Bis{[4-(1',1',1',3',5',5',5'-heptamethyltrisiloxy-2''-methylpropyloxy)-2-hydroxy]phenyl}-6-(4-methoxyphenyl)-1,3,5-triazine | 2 g |
| Benzotriazole silicone of formula (I') in which: r = 0; s = 1 and D = —CH$_2$—CH(CH$_3$)—CH$_2$— | 3 g |
| Glycerol | 15 g |
| Preservatives | qs |
| Demineralized water qs | 100 g |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition suited for the photoprotection of human skin and/or hair, comprising an effective sunscreening and water-resistant amount of combinatory immixture of (a) at least one silicone benzotriazole first sunscreen compound having the formula (I'):

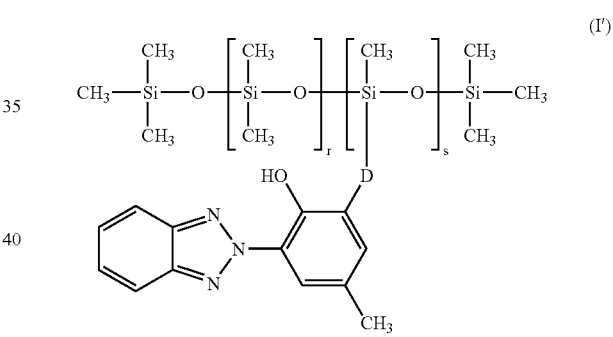

wherein r=0, s=1 and

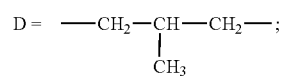

and (b) at least one bis-resorcinyl triazine second sunscreen compound which is 2,4-bis{[4-(2-ethylhexyloxy)-2-hydroxy]phenyl}-6-(4-methoxyphenyl)-1,3,5-triazine; formulated into (c) a topically applicable, cosmetically acceptable vehicle, diluent or carrier therefor;

wherein (a) and (b) are each present in an amount of from 0.1% to 15% by weight relative to the total weight of the composition.

2. The composition according to claim 1, wherein (a) and (b) are each present in an amount of from 0.1% to 10% by weight relative to the total weight of the composition.

3. The composition according to claim 1, wherein (a) and (b) are each present in an amount of from 0.2% to 10% by weight relative to the total weight of the composition.

4. The composition according to claim 1, formulated as an oil-in-water emulsion.

5. The composition according to claim 1, further comprising at least one additional hydrophilic or lipophilic organic UV-A and/or UV-B sunscreen.

6. The composition according to claim 5, further comprising at least one cinnamic derivative, salicylic derivative, camphor derivative, triazine derivative, benzophenone derivative, dibenzoylmethane derivative, benzimidazole derivative, β, β-diphenylacrylate derivative or p-aminobenzoic acid derivative sunscreen or sunscreen polymer, or sunscreen silicone.

7. The composition according to claim 1, further comprising a photoprotecting effective amount of particulates of at least one coated or uncoated inorganic pigment or nanopigment.

8. The composition according to claim 7, said at least one pigment or nanopigment comprising titanium dioxide, zinc oxide, iron oxide, zirconium oxide, cerium oxide, or mixture thereof.

9. The composition according to claim 1, further comprising at least one active agent for the artificially tanning and/or browning of human skin.

10. The composition according to claim 1, further comprising at least one cosmetically acceptable adjuvant or additive.

11. The composition according to claim 10, said at least one adjuvant or additive comprising a fat, organic solvent, thickening agent, softener, antioxidant, opacifying agent, stabilizing agent, emollient, hydroxy acid, anti-foaming agent, hydrating agent, vitamin, fragrance, preservative, surfactant, filler, sequestering agent, polymer, propellant, basifying or acidifying agent, dye, colorant, or mixture thereof.

12. The composition according to claim 1, comprising a nonionic vesicular dispersion, emulsion, cream, milk, gel, cream gel, ointment, suspension, dispersion, powder, solid stick or tube, foam or spray.

13. The composition according to claim 1, comprising a makeup.

14. The composition according to claim 13, comprising an anhydrous or aqueous solid or paste, emulsion, suspension or dispersion.

15. The composition according to claim 1, comprising a shampoo, lotion, gel, nonionic vesicular dispersion, hair lacquer, or rinse.

16. A regime/regimen for protecting human skin and/or hair against the deleterious effects of ultraviolet irradiation, comprising topically applying thereto an effective amount of the topically applicable sunscreen/cosmetic composition according to claim 1.

* * * * *